(12) United States Patent
Sarkas et al.

(10) Patent No.: US 11,155,683 B2
(45) Date of Patent: Oct. 26, 2021

(54) LIPOPHILLICALLY DISPERSED PHENOLIC POLYMER PARTICLES

(71) Applicant: Nanophase Technologies Corporation, Romeoville, IL (US)

(72) Inventors: Harry W. Sarkas, Shorewood, IL (US); Christopher C. Boffa, Joliet, IL (US); Kevin Cureton, Evanston, IL (US)

(73) Assignee: Nanophase Technologies Corporation, Romeoville, IL (US)

( * ) Notice: Subject to any disclaimer, the term of this patent is extended or adjusted under 35 U.S.C. 154(b) by 0 days.

(21) Appl. No.: 16/570,944

(22) Filed: Sep. 13, 2019

(65) Prior Publication Data

US 2021/0079174 A1 Mar. 18, 2021

(51) Int. Cl.
| | | |
|---|---|---|
| C08J 3/12 | (2006.01) | |
| A61K 8/02 | (2006.01) | |
| A61K 8/84 | (2006.01) | |
| A61Q 17/04 | (2006.01) | |
| C08J 3/09 | (2006.01) | |

(52) U.S. Cl.
CPC .......... *C08J 3/126* (2013.01); *A61K 8/0225* (2013.01); *A61K 8/84* (2013.01); *A61Q 17/04* (2013.01); *C08J 3/095* (2013.01); *C08J 3/098* (2013.01); *A61K 2800/412* (2013.01); *A61K 2800/413* (2013.01); *A61K 2800/622* (2013.01); *C08J 2397/00* (2013.01)

(58) Field of Classification Search
CPC ... C08J 3/126; C08J 3/098; C08J 3/095; C08J 2397/00; A61Q 17/04; A61K 8/84; A61K 8/0225; A61K 2800/622; A61K 2800/413; A61K 2800/412
See application file for complete search history.

(56) References Cited

U.S. PATENT DOCUMENTS

| | | | | |
|---|---|---|---|---|
| 6,500,411 B2 * | 12/2002 | SenGupta | ................ | A61K 8/26 424/59 |
| 6,716,418 B2 | 4/2004 | SenGupta et al. | | |
| 8,277,557 B2 * | 10/2012 | Reknes | ................ | A23K 20/111 106/726 |
| 8,309,063 B2 | 11/2012 | SenGupta et al. | | |
| 8,445,562 B2 | 5/2013 | Balakshin et al. | | |
| 8,911,976 B2 | 12/2014 | Uraki et al. | | |
| 10,035,928 B2 | 7/2018 | Liu et al. | | |
| 2006/0280702 A1 * | 12/2006 | SenGupta | ............ | A61K 8/8147 424/59 |
| 2007/0178057 A1 | 8/2007 | SenGupta et al. | | |
| 2010/0202985 A1 * | 8/2010 | SenGupta | ................ | A61K 8/72 424/59 |
| 2015/0166836 A1 | 6/2015 | Liu et al. | | |
| 2018/0291210 A1 | 10/2018 | Sarkas et al. | | |

FOREIGN PATENT DOCUMENTS

| | | |
|---|---|---|
| CN | 108456314 | 8/2018 |
| WO | 2002/062310 | 8/2002 |
| WO | 2006/135463 | 12/2006 |
| WO | 2009/038477 | 3/2009 |
| WO | 2014/144746 | 9/2014 |
| WO | 2014/164418 | 10/2014 |
| WO | 2017/197530 | 11/2017 |
| WO | 2021/050436 | 3/2021 |

OTHER PUBLICATIONS

Pan, X. et al., "Organosols ethanol lignin from hybrid poplar as a radical scavenger: Relationship between lignin structure, extraction conditions, and antioxidant activity", Journal of Agricultural and Food Chemistry, vol. 54, pp. 5806-5813, (2006).
Cosmetics Europe, "Guidelines for evaluating sun product water resistance", available online at www.cosmeticseurope.eu/files/7914/6407/7400/Guidelines_for_Evaluating_Sun_Product_Water_Resistance_-_2005.pdf, 15 pages (2005).
Bleasel, M.D. et al., "In vitro evaluation of sun protection factors of sunscreen agents using a novel UV spectrophotometric technique", International Journal of Cosmetic Science, vol. 30, issue 4, pp. 259-270, (2008).
International Search Report and Written Opinion dated Mar. 11, 2021 for PCT application No. PCT/US2020/049742.
Vinardell, M.P. et al., "Potential applications of antioxidant lignins from different sources", Industrial Crops and Products, vol. 27, No. 2, pp. 220-223, (2008).
Definition of "Lignin" printed from Wikipedia, the free encyclopedia on Aug. 22, 2019 found at http://en.wikipedia.org/wiki/Lignin.

\* cited by examiner

*Primary Examiner* — Matthew P Coughlin
*Assistant Examiner* — Thurman Wheeler
(74) *Attorney, Agent, or Firm* — Evan Law Group LLC

(57) ABSTRACT

A composition comprises phenolic polymer particles and a surfactant, on the phenolic polymer particles. The composition is lipophilic. A dispersion comprises the phenolic polymer particles, the surfactant, and a carrier vehicle. The carrier vehicle may be a cosmetically-acceptable fluid or a wax that is lipophilic.

24 Claims, 1 Drawing Sheet

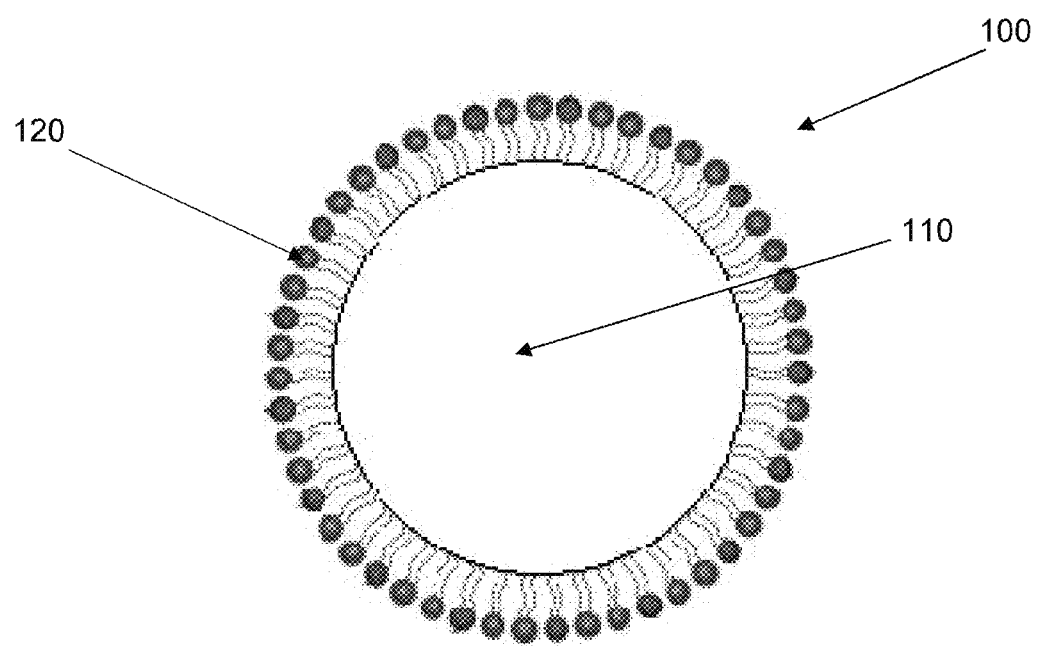

LIPOPHILLICALLY DISPERSED PHENOLIC POLYMER PARTICLES

BACKGROUND

Phenolic polymers are a class of organic polymers that are characterized by the presence of a plurality of OH-substituted phenyl groups. Phenolic polymers have a number of unique properties, such as the ability to function as antioxidants or skin conditioning agents. These properties have led to phenolic polymers being included in topically-applied formulations such as cosmetics and dermatological preparations. Well known examples of phenolic polymers include lignin, lignosulfonate salts, humates and tannins.

Lignin is a particularly desirable phenolic polymer because of its ubiquity. The modern paper manufacturing process involves the removal of lignin from lignocellulose. The global paper manufacturing industry produces about 40-50,000,000 tons of lignin annually as a waste product (The International Lignin Institute, "About lignin", available online at www.ili-lignin.com/aboutlignin.php (accessed Aug. 30, 2019)). Lignin is also produced as a byproduct of sulfite pulping to remove lignin from wood pulp. The waste lignin is typically burned to provide energy for the paper manufacturing plant where it is generated. Processes have been developed to transform waste lignosulfonates and kraft lignins into useful commodities. For example, high quality lignin may be obtained from the black liquor produced in the kraft process for paper manufacturing using the LIGNOBOOST® process or the LIGNOFORCE® process. However, there are still tens of millions of tons of waste lignin produced every year that could be converted into useful chemical products.

Despite their availability as raw materials, formulation challenges have limited the demand for phenolic polymers. Lignin and other phenolic polymers are highly soluble in water. As a result, phenolic polymers have only been included in the water phase of formulations. The high water solubility of phenolic polymers also limits their inclusion in topical formulations in the solid state since the phenolic polymers will wash off the skin of a user if exposed to water. These solubility concerns have restricted the ability of manufacturers to take full advantage of the useful properties of phenolic polymers.

SUMMARY

In a first aspect, the invention is a composition comprising phenolic polymer particles and a surfactant, on the phenolic polymer particles.

In a second aspect, the invention is a dispersion comprising sodium lignosulfonate particles, a surfactant and a carrier vehicle. The sodium lignosulfonate particles have a particle size of 0.1-1.0 microns. The dispersion is pourable.

In a third aspect, the invention is a dispersion comprising a silanized phenolic polymer particle and a carrier vehicle.

In a fourth aspect, the invention is lipophilic phenolic polymer particles.

Definitions

The term "phenolic polymer" means a water-soluble polymer that includes a plurality of OH-substituted phenyl groups. Examples of phenolic polymers include lignins, humates, tannins and botanical extracts containing water soluble and/or water dispersible components.

The term "ultraviolet radiation" means electromagnetic radiation with a wavelength of 10-400 nm. Ultraviolet radiation is also referred to as ultraviolet light, UV radiation or UV light. The abbreviation "UV" is used interchangeably with the phrase "ultraviolet light" in the application.

The term "high energy visible radiation" or "HEV radiation" means electromagnetic radiation having a wavelength of 400-490 nm. HEV radiation is perceived as blue and violet light in the visible spectrum.

The term "particle size" means the median (D50) particle size as determined by static light scattering (ISO 13320: 2009 Particle Size Analysis—Laser Diffraction Methods) on a number distribution basis, unless otherwise indicated.

The term "very water resistant" means a composition that exhibits a change in monochromatic protection factor (MPF) of less than 50% between its MPF prior to water exposure and its MPF following an 80-minute water immersion sequence in vitro. (Cosmetics Europe, "Guidelines for evaluating sun product water resistance", available online at www.cosmeticseurope.eu/files/7914/6407/7400/Guidelines_for_Evaluating_Sun_Produc t_Water_Resistance_-_2005.pdf, 15 pages (2005)).

The "modified DPPH photostability test" is a measure of the photostability of an active material. The modified DPPH photostability test is a more sensitive test than the DPPH photostability test described in US Patent Application Publication No. 2018/0291210 and has been validated for compositions beyond zinc oxide. First, 0.025 g±0.001 g of active material is added to four 50 mL disposable plastic beakers. 0.0125% DPPH (di(phenyl)-(2,4,6-trinitrophenyl) iminoazanium, also referred to as diphenylpicrylhydrazyl; CAS Number 1898-66-4) is prepared in BCS (ethylene glycol butyl ether) solution. 19.975 g±0.001 of 0.0125% DPPH in BCS solution is added to each beaker containing the active material to form a test mixture. The test mixtures are thoroughly stirred with a glass stir rod, and each test mixture is sonicated for 20 seconds to ensure that the active material is well-dispersed. After sonication, each test mixture is transferred to a labelled scintillation vial. The absorbance of the test mixtures is measured on a calibrated colorimeter to obtain a pre-irradiation measurement. After taking the measurements, the test mixtures are exposed to UV light in a Q-Labs QUV Weatherometer using UVA bulbs at 0.35 $Wm^{-2}\ s^{-1}$ at a constant temperature of 50° C. for 10 minutes. After irradiation, the absorbance of the test mixtures is measured on the colorimeter. Photostability following UV exposure is determined by the persistence of a purple color due to the absorption band of the dye at 520 nm.

Photostability may be expressed as the total color change relative to a standard ($\Delta E$ in L*a*b* color space) for a stated UV exposure time. $\Delta E$ is calculated from Equation 1 below, as per the International Commission on Illumination Standard CIE76 definition:

$$\Delta E = \sqrt{(L^*_2 - L^*_1)^2 + (a^*_2 - a^*_1)^2 + (b^*_2 - b^*_1)^2} \qquad \text{Equation 1}$$

where $L^*_2$, $a^*_2$ and $b^*_2$ are the color coordinates of test mixture after irradiation and $L^*_1$, $a^*_1$ and $b^*_1$ are the color coordinates of test mixture prior to irradiation. Data is reported as the average $\Delta E$ value of the four samples.

The term "super photostable" means a substance that has a $\Delta E \leq 4.5$ when subjected to the modified DPPH photostability test.

The "free radical quenching test" is a measure of the ability of an active material to quench free radicals. First, the photostability of titanium dioxide (35 nm, rutile phase) is measured according to the modified DPPH photostability test to establish a reference photostability ($\Delta E_{Ref}$). Next, a test mixture is prepared containing the same weight percentage of titanium dioxide used to establish the reference photostability and an equal amount of an active material. The photostability of the test mixture is then measured according to the modified DPPH photostability test to establish a test photostability ($\Delta E_{Test}$). Then, the percentage difference between the reference photostability ($\Delta E_{Ref}$) and the test photostability ($\Delta E_{Test}$) is calculated to determine the free radical quenching ability of the active material. An active material passes the free radical quenching test if it quenches at least 70% of the free radicals produced by the titanium dioxide ($\Delta E_{Test}$ is at least 70% less than $\Delta E_{Ref}$).

All percentages (%) are weight/weight percentages, unless stated otherwise.

BRIEF DESCRIPTION OF THE DRAWINGS

The invention can be better understood with reference to the following drawings and description.

FIG. 1 is a cartoon representation of a phenolic polymer particle that has been modified with a surfactant.

DETAILED DESCRIPTION

The present invention includes phenolic polymer particles that have been modified to be lipophilic. Lipophilic phenolic polymer particles may be formed by adding a surface treatment to the particles or by reacting the particles with a silanizing agent. The lipophilic modification enables the phenolic polymers to be present in the solid state in the oil phase of formulations. For example, phenolic polymer particles and a surfactant may be dispersed in a lipophilic carrier vehicle. The ability to use phenolic polymer particles in the oil phase greatly expands the possible uses of these particles.

Experimental tests have revealed that preparations including lipophilic phenolic polymer particles possess a number of desirable physical and chemical properties. These preparations are very water resistant and are strong HEV light blockers, which indicates they are well-suited for use in sunscreen formulations. The preparations also are super photostable when subjected to the modified DPPH photostability test. In addition, the preparations pass the free radical quenching test, which illustrates their strong antioxidant capabilities.

Without wishing to be bound by theory, it is believed that these properties result from the presence of the phenolic polymers in the solid state. Physical interactions between phenolic polymer molecules result in pi ($\pi$) stacking of the aromatic groups, which improves the ability of these molecules to accept electrons because of orbital mixing. Although pi stacking can occur when the phenolic polymers are in solution, the solution must have a sufficiently high concentration. Delivering the phenolic polymers as particles (that is, in the solid state) ensures that they have pi stacking.

Preparations that include phenolic polymer particles also offer a number of commercial advantages. Phenolic polymers, particularly lignin, are economically-favorable raw materials since they are available in substantial quantities as waste products. Capturing a waste product that would otherwise be combusted is an environmentally-friendly process since it prevents carbon emissions. Phenolic polymers that are derived from natural sources may be marketed as natural products, which is particularly attractive to consumers. Furthermore, dispersions of phenolic polymer particles may be manufactured using conventional chemical processing techniques that do not require expensive reactants, extreme temperatures, long reaction times or hazardous reactants, and do not produce hazardous wastes. All of these advantages will encourage manufacturers to include phenolic polymers in commercial formulations.

FIG. 1 illustrates a cartoon representation of a phenolic polymer particle that has been modified with a surfactant. A composition 100 includes a phenolic polymer particle 110 and a surfactant 120 on the surface of the particle. The surfactant is a surface treatment that makes the phenolic polymer particle lipophilic and resistant to dissolution in water. A dispersion may be prepared by combining the phenolic polymer particles, the surfactant and a carrier vehicle. Preferably, the dispersion is pourable.

The phenolic polymer particles may be any polymer having a plurality of OH-substituted phenyl groups. Preferably, the phenolic polymer particles are lignins, humates, tannins, botanical extracts containing water soluble and/or water dispersible components, or combinations thereof. Examples of suitable lignins include lignosulfonate, kraft lignin, sulfonated kraft lignin, oxylignin, sulfonated oxylignin, lignosulfonate copolymerized with monomers such as acrylate, acrylic acid, acrylamide, styrene sulfonate, and naphthalene sulfonate derivatives, azoligno-sulfonate, azolignin, lignosulfonate-formaldehyde condensates, lignin formaldehyde condensates, hydrophobically modified lignosulfonate, hydrophobically-modified lignin, cationically-modified lignosulfonate, cationically-modified lignin, amino lignosulfonate, amino lignin, alkylated lignosulfonate, alkylated lignin, crosslinked lignosulfonate and crosslinked lignin. Examples of suitable humates include sulfonated humate, humate-formaldehyde condensates, hydrophobically-modified humate, cationically-modified humate, amino humate and alkylated humate. Examples of suitable tannins include tannate, sulfonated tannate, tannate-formaldehyde condensates, hydrophobically modified tannate and cationically-modified tannate.

Examples of botanical extracts containing water soluble and/or water dispersible components include extracts derived from plants known as *Acacia, Afzelia, Synsepalum duloificum, Albizie*, alder (for example, *Alnus glutinosa* and *Alnus rubra*), applewood, *Arbutus*, ash (for example, *F. nigra, F. quadrangulata, F. excelsior, F. pennsylvanica lanceolata, F. latfolia, F. profinda* and *F. americana*), aspen (for example, *P. grandidentata, P. tremula* and *P. tremuloides*), Australian red cedar (*Toona ciliata*), ayan (*Distemonanthus benthamianus*), balsa (*Ochroma pyramidale*), basswood (for example, *T. Americana* and *T. heterophylla*), beech (for example, *F. Syvatica* and *F. grandifolia*), birch (for example, *Betula populifolia, B. nigre, B. papyrifera, B. lenta, B. alleghaniensis/B. lutea, B. pendula* and *B. pubescens*), blackbean, blackwood, bocote, boxelder, boxwood, brazilwood, bubinga, buckeye (for example, *Aesculus hippocastianum, Aesculus glabra* and *Aesculus flava/Aesculus octandra*), butternut, catalpa, cherry (for example, *Prunus serotina, Prunus pennsylvanica* and *Prunus avium*), crabwood, chestnut, coachwood, cocobolo, corkwood, cottonwood (for example, *Populus balsamifera, Populus deltoides, Populus sargentii* and *Populus heterophyll*), cucumber tree, dogwood (for example, *Comus florida* and *Comus nuttallii*), ebony (for example, *Diospyros kurzii, Diospyros melanida* and *Diospyros crassiflora*), elm (for example, *Ulmus americana, Ulmus procera, Ulmus thomasii, Ulmus rubra* and *Ulmus glabra*), eucalyptus, greenheart, grenadilla, gum (for example, *Nyssa sylvatica, Eucalyptus globulus, Liquidambar styraciflua* and *Nyssa aquatica*), hickory (for example, *Carya alba, Carya glabra, Carve ovate* and *Carya laciniosa*), hornbeam, hophornbeam, ipe, iroko, ironwood (for example, *Bangkirai, Carpinus caroliniana, Casuarina equisetifolia, Choricbangarpia subargentea, Copaifera* spp., *Eusideroxylon zwageri, Guaiacum officinale, Guaiacum sanctum, Hopea odorata, Krugiodendron ferreum, Lyonothamnus ivonii* (*L. floribundus*), *Mesua ferrea, Olea* spp., *Olneya tesota, Ostrya virginiana, Parrotia persica* and *Tabebuia serratifolia*), jacaranda, jojoba, lacewood, laurel, limba, Lignum vitae, locust (for example, *Robinia pseudacacia* and *Gleditsia triacanthos*), mahogany, maple (for example, *Acer saccharum, Acer nigrum, Acer negundo, Acer rubrum, Acer Saccharinum* and *Acer pseudoplatanus*), meranti, mpingo, oak (for example, *Quercus macrocarpa, Quercus alba, Quercus stellata, Quercus bicolor, Quercus virginiana, Quercus michauxii, Quercus prinus, Quercus muhlenbergii, Quercus chrysolepis, Quercus lyrata, Quercus robur, Quercus petraea, Quercus rubra, Quercus velutina, Quercus laurifolia, Quercus falcata, Quercus nigra, Quercus phellos* and *Quercus texana*), obeche, okoumé, Oregon myrtle, California bay laurel, pear, poplar (for example, *P. balsamifera, P. nigra* and hybrid poplar (*PopulusX canadensis*)), ramin, red cedar, rosewood, sal, sandalwood, sassafras, satinwood, silky oak, silver wattle, snakewood, sourwood, Spanish cedar, American sycamore, teak, walnut (for example, *Juglans nigra* and *Juglans regia*), willow (for example, *Salix nigra* and *Salix alba*), yellow poplar (*Liriodendron tulipifera*), *Araucaria* (for example, *A. cunninghamii, A. angustifolia* and *A. araucana*), softwood cedar (for example, *Juniperus virginiana, Thuja plicata, Thuja occidentalis, Chamaecyparis thyoides* and *Callitropsis nootkatensis*), cypress (for example, *Chamaecyparis, Cupressus taxodium, Cupressus arizonica, Taxodium distichum, Chamaecyparis obtusa, Chamaecyparis lawsoniana* and *Cupressus sempervicen*), Rocky Mountain Douglas fir, European yew, fir (for example, *Abies balsamea, Abies alba, Abies procera* and *Abies amabilis*), hemlock (for example, *Tsuga Canadensis, Tsuga mertensiana* and *Tsuga heterophylla*), kauri, kaya, larch (for example, *Larix decidua, Larix kaempferi, Larix laricina, Larix occidentalis* and *Larix europea*), pine (for example, *Pinus nigra, Pinus banksiana, Pinus contorta, Pinus radiata, Pinus ponderosa, Pinus resinosa, Pinus sylvestris, Pinus strobus, Pinus monticola, Pinus lambertiana, Pinus taeda, Pinus palustris, Pinus rigida* and *Pinus echinata*), redwood, rimu, spruce (for example, *Picea abies, Picea mariana, Picea rubens, Picea sitchensis* and *Picea glauca*), sugi and mixtures/hybrids thereof. Preferred botanical extracts containing water soluble and/or water dispersible components include extracts derived from *Picea abies* (also known as Norway spruce or European spruce), *Larix europaea* (also known as larch or European larch), and a mixture of the maple species *Acer saccharum, Acer Saccharinum* and *Acer negundo*.

The surfactant may be any surfactant that has strong acid-base interactions with the phenolic polymer particles and provides a lipophilic surface treatment on the particles. Examples of suitable surfactants include fatty alcohols and polyols (for example, stearyl alcohol, behenyl alcohol and cetearyl alcohol), fatty acids (for example, stearic acid and oleic acid), amino acids (for example, lauroyl lysine and myristoyl glutamate), polyglyceryl esters (for example, polyglyceryl-3 ricinoleate, polyglyceryl-6 ricinoleate, polyglyceryl-10 pentastearate and polyglyceryl-4 oleate), polyglyceryl polyesters (for example, polyglyceryl-4 diisostearate/polyhydroxystearate/sebacate, polyglyceryl-2 dipolyhydroxystearate and polyglyceryl-3 stearate/isostearate/dimer dilinoleate crosspolymer), polyesters with affinic hydroxyl, amine or amide groups (for example, polyhydroxystearic acid), polyurethanes with affinic hydroxyl, amine or amide groups, polyamides with affinic hydroxyl, amine or amide groups, polyacrylates with affinic hydroxyl, amine or amide groups, phosphate esters (for example, trilaureth-4 phosphate and triceteareth-4 phosphate), polymeric phosphoric acid salts (for example, 1,2-ethanediamine, polymers with aziridine, N-[3-[(2-ethylhexyl)oxy]-3-oxypropyl]derivatives and compounds including polyethylene-polypropylene glycol), phospholipids, ceramides, sphingosides (for example, lecithin, lysolecithin and ceramide 3), substituted silicones with affinic groups (for example, cetyl diglyceryl tris(trimethylsiloxy)silylethyl dimethicone, CAS Number 104780-66-7 (Siloxanes and Silicones, di-Me, 3-hydroxypropyl group-terminated), CAS Number 102782-61-6 (Siloxanes and Silicones, di-Me, 3-hydroxypropyl Me) and CAS Number 106214-84-0 (Siloxanes and silicones, dimethyl, 3-aminopropyl)) and combinations thereof.

Alternatively, lipophilic phenolic polymer particles may be formed by reacting the particles with a silanizing agent. The silanizing agent may be any substance that provides functionalized polysiloxanes on the surface of the phenolic polymer particles. Examples of suitable silanizing agents include reactive silicone and silane hydrophobizing surface treatments (for example, triethoxycaprylysilane, octadecyltriethoxysilane, hydrogen dimethicones (CAS Numbers 68037-59-2/69013-23-6/70900-21-9) and CAS Number 69430-47-3 (Siloxanes and Silicones, di-Me, reaction products with Me hydrogen siloxanes and 1,1,3,3-tetramethyldisiloxane)).

The carrier vehicle may be any cosmetically-acceptable fluid or wax that is lipophilic. Examples of suitable carrier vehicles include triglycerides (for example, caprylic/capric triglycerides), esters (for example, C12-C15 alkyl benzoate, isopentyl laurate, isopropyl isostearate, coco-caprylate, ethylhexyl isononanoate, tridecyl salicylate, ethylhexyl isononanoate, isodecyl salicylate, octyldodecyl neopentanoate, butyloctyl salicylate, jojoba esters and shea butter ethyl esters), natural oils and butters (for example, *Simmondsia chinensis* (jojoba) seed oil, shea butter, *Argania spinosa* (Argan) oil, pongami (karanja) oil and *Limnanthes alba* (white meadowfoam) seed oil), alkanes (for example, squalane, hemisqualane, isododecane and isohexadecane), silicones (for example, dimethicone, behenyl dimethicone, cetyl dimethicone, cetearyl methicone and phenyl dimethicone), waxes (for example, natural waxes, synthetic waxes and silicone waxes) and combinations thereof.

The phenolic polymer particles may be present in the dispersion in an amount of 0.1-75.0% by weight, including 0.2%, 0.3%, 0.4%, 0.5%, 0.6%, 0.7%, 0.8%, 0.9%, 1.0%, 2.0%, 3.0%, 4.0%, 5.0%, 6.0%, 7.0%, 8.0%, 9.0%, 10.0%, 15.0%, 20.0%, 25.0%, 30.0%, 35.0%, 40.0%, 45.0%, 50.0%, 55.0%, 60.0%, 65.0% and 70.0% by weight. Preferably, the phenolic polymer particles are present in an amount of 0.5-50.0% by weight. More preferably, the phenolic polymer particles are present in an amount of 1.0-40.0% by weight.

The surfactant may be present in the dispersion in an amount of 1.0-100.0% of the mass of phenolic polymer particles, including 1.1%, 1.2%, 1.3%, 1.4%, 1.5%, 1.6%, 1.7%, 1.8%, 1.9%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0%, 15.0%, 20.0%, 25.0%, 30.0%, 35.0%, 40.0%, 45.0%, 50.0%, 55.0%, 60.0%, 65.0%, 70.0%, 75.0%, 80.0%, 85.0%, 90.0% and 95.0% of the mass of the phenolic polymer particles. Preferably, the surfactant is present in an amount of 10.0-60.0% of the mass of the phenolic polymer particles. More preferably, the surfactant is present in an amount of 20.0-50.0% of the mass of the phenolic polymer particles.

The amount of carrier vehicle in the dispersion will be dependent on the amount of the phenolic polymer particles and the amount of the surfactant present in the dispersion. After combining the phenolic polymer particles and the surfactant, the carrier vehicle may be added in any suitable amount necessary to produce a desired dispersion.

The dispersion may be prepared by conventional formulation techniques. For example, the phenolic polymer particles, the surfactant and the carrier vehicle may be combined in a vessel and stirred until homogenous. Appropriate mixing conditions such as temperature, stirring speed and mixing time, may be varied to provide a desired dispersion. The dispersion may then be transferred to a mill, such as a media mill, and comminuted to achieve a desired particle size.

The phenolic polymer particles may have a particle size of 0.001-10.0 microns ($\mu$m) (1-10,000 nm), including 0.002 $\mu$m, 0.003 $\mu$m, 0.004 $\mu$m, 0.005 $\mu$m, 0.006 $\mu$m, 0.007 $\mu$m, 0.008 $\mu$m, 0.009 $\mu$m, 0.01 $\mu$m, 0.02 $\mu$m, 0.03 $\mu$m, 0.04 $\mu$m, 0.05 $\mu$m, 0.06 $\mu$m, 0.07 $\mu$m, 0.08 $\mu$m, 0.09 $\mu$m, 0.1 $\mu$m, 0.2 $\mu$m, 0.3 $\mu$m, 0.4 $\mu$m, 0.5 $\mu$m, 0.6 $\mu$m, 0.7 $\mu$m. 0.8 $\mu$m, 0.9 $\mu$m, 1.0 $\mu$m, 1.1 $\mu$m, 1.2 $\mu$m, 1.3 $\mu$m, 1.4 $\mu$m, 1.5 $\mu$m, 1.6 $\mu$m, 1.7 $\mu$m, 1.8 $\mu$m, 1.9 $\mu$m, 2.0 $\mu$m, 2.5 $\mu$m, 3.0 $\mu$m, 3.5 $\mu$m, 4.0 $\mu$m, 4.5 $\mu$m, 5.0 $\mu$m, 5.5 $\mu$m, 6.0 $\mu$m, 6.5 $\mu$m, 7.0 $\mu$m, 7.5 $\mu$m, 8.0 $\mu$m, 8.5 $\mu$m, 9.0 $\mu$m and 9.5 $\mu$m. Preferably, the phenolic polymers have a particle size of 0.01-5.0 $\mu$m (10-5,000 nm). More preferably, the phenolic polymers have a particle size of 0.1-1.0 $\mu$m (100-1,000 nm). The maximum particle size of the phenolic polymer particles is 10.0 $\mu$m to prevent perception of the particles on the skin and avoid formulations that have a gritty or grainy texture to users.

Lipophilic phenolic polymer particles may be obtained from a dispersion of phenolic polymer particles, a surfactant and a carrier vehicle by removing the carrier vehicle. For example, the carrier vehicle may be a volatile substance that evaporates at ambient temperature and pressure. Similarly, the dispersion may be heated above the boiling point of the carrier vehicle until the carrier vehicle is removed.

Lipophilic phenolic polymer particles also may be prepared directly rather than by isolation from a dispersion. First, the particle size of the phenolic polymer particles is reduced by dry comminution. Any suitable dry comminution technique may be used, such as high performance air milling, vibratory milling, media milling, hammer milling and jet milling. The comminution may be carried out neat or in conjunction with a secondary material such as a polymer particle or an oxide (for example, metal oxides and silicates such as mica or silica). Next, a solution is prepared by dissolving the surfactant or silanizing agent into a suitable solvent. Examples of suitable solvents include USP heptane, USP acetone, USP isopropanol and USP ethanol. Then, the solution is sprayed onto the comminuted phenolic polymer particles in a blender/mixer under agitation. The solution and comminuted phenolic polymer particles may optionally be heated to drive a reaction for binding the surfactant or silanizing agent to the particles. Finally, a vacuum is applied to remove the solvent.

Lipophilic phenolic polymer particles may be present in the oil phase of a preparation, or may be added to a powder preparation. Preferably, the preparation is suitable for topical application. Examples of suitable preparations include emulsions (oil-in-water and water-in-oil emulsions), sprays, balms, sticks, powders, powder-to-cream preparations, lipophilic preparations and anhydrous preparations. Preparations including lipophilic phenolic polymer particles may be evaluated by one or more tests. Preferably, preparations including lipophilic phenolic polymer particles are very water resistant, super photostable and pass the free radical quenching test.

Preparations containing lipophilic phenolic polymer particles may be formulated for use in a variety of different applications. Examples of suitable formulations include cosmetics (for example, blushes, face powders, foundations, lipsticks, makeup bases and rouges), skin care products (for example, skin cleansing creams, lotions, liquids and pads; face and neck creams, lotions, powders and sprays; body and hand creams, lotions, powders and sprays; foot powders and sprays; moisturizers; night creams, lotions, powders and sprays; paste masks/mud packs; and skin fresheners) and sunscreens. Sunscreens are particularly preferred formulations. The formulations may be provided in any form suitable for topical administration, such as in the form of a topical suspension, lotion, cream, ointment, gel, hydrogel, foam, paste, tincture, liniment, sprayable liquid, aerosol, stick or powder. The formulations may optionally include inactive ingredients, auxiliaries and/or additives such as co-emulsifiers, fats, waxes, stabilizers, thickeners, biogenic active ingredients, film formers, fragrances, dyes, pearlizing agents, preservatives, pigments, electrolytes and pH regulators.

A sunscreen may include lipophilic phenolic polymer particles and a UV radiation protectant. The UV radiation protectant may be any substance that absorbs, reflects and/or scatters UV radiation. The sunscreen may optionally include sun protection factor (SPF) boosters or stabilizers such as methoxycrylene and polyester-8.

Examples of suitable UV radiation protectants include zinc oxide (ZnO), titanium dioxide ($TiO_2$), p-aminobenzoic acid (PABA), padimate O (OD-PABA, octyldimethyl-PABA, $\sigma$-PABA), phenylbenzimidazole sulfonic acid (ensulizole, EUSOLEX® 232, PBSA, PARSOL® HS), cinoxate (2-ethoxyethyl p-methoxycinnamate), dioxybenzone (benzophenone-8), oxybenzone (benzophenone-3, EUSOLEX® 4360, ESCALOL® 567), homosalate (homomethyl salicylate, HMS), menthyl anthranilate (meradimate), octocrylene (EUSOLEX® OCR, 2-cyano-3,3-diphenyl acrylic acid, 2-ethylhexylester), octyl methoxycinnamate (octinoxate, EMC, OMC, ethylhexyl methoxycinnamate, ESCALOL® 557, 2-ethylhexyl-paramethoxycinnamate, PARSOL® MCX), octyl salicylate (octisalate, 2-ethylhexyl salicylate, ESCALOL® 587), sulisobenzone (2-hydroxy-4-methoxybenzophenone-5-sulfonic acid, 3-benzoyl-4-hydroxy-6-methoxybenzenesulfonic acid, benzophenone-4, ESCALOL®577), trolamine salicylate (triethanolamine salicylate), avobenzone (1-(4-methoxyphenyl)-3-(4-tert-butylphenyl)propane-1,3-dione, butyl methoxy dibenzoylmethane, BMDBM, PARSOL® 1789, EUSOLEX® 9020), ecamsule (MEXORYL® SX, terephthalylidene dicamphor sulfonic acid), cerium oxide ($CeO_2$), drometrizole trisiloxane (MEXORYL® XL), bis-ethylhexyloxyphenol methoxyphenyl triazine (TINOSORB® S), bisoctrizole (TINOSORB® M, MILESTAB™ 360) and combinations thereof. Preferred UV radiation protectants include zinc oxide (ZnO), titanium dioxide ($TiO_2$) and combinations thereof. Preferably, the UV radiation protectant has been approved by at least one of the regulatory agencies of the United States (U.S. Food and Drug Administration or FDA), Canada, the European Union, Australia, Japan, Korea, China, Mercosur, the Association of Southeast Asian Nations (ASEAN), the Commonwealth of Independent States (CIS) and the Gulf Cooperation Council (GCC).

Sunscreens that include lipophilic phenolic polymer particles offer a number of advantages as compared to conventional sunscreens. The inclusion of phenolic polymer particles produces sunscreens that are very water resistant. In addition, the phenolic polymer particles allow the sunscreen to block or attenuate both UV radiation and HEV radiation. The phenolic polymer particles also are resistant to photo-induced free radical generation by UV radiation and HEV radiation.

Formulations that include lipophilic phenolic polymer particles provide a variety of health benefits. Phenolic polymer particles act as antioxidants because they are extremely efficient at neutralizing free radicals. These properties allow phenolic polymer particles to treat or prevent oxidative stress or damage to the skin, hair and nails. For example, the phenolic polymer particles may be used to protect keratinous material (such as the hair, fingernails, toenails and the outer layer of skin), protect human skin, suppress lipid peroxidation, prevent or reduce lines and wrinkles on the skin, prevent loss of elasticity of the skin, prevent thinning of the skin and prevent pigment darkening of the skin. These health benefits may be obtained by applying a formulation containing lipophilic phenolic polymer particles to an area of skin.

EXAMPLES

Example 1

Dispersion of Sodium Lignosulfonate and Polyglyceryl-2 Dipolyhydroxystearate in Caprylic/Capric Triglycerides 30.0 parts by weight of sodium lignosulfonate (Vanisperse A, Borregaard LignoTech) was combined with 10.5 parts by weight of polyglyceryl-2 dipolyhydroxystearate and 59.5 parts by weight of caprylic/capric triglycerides. The mixture was stirred until homogenous and transferred to a horizontal media mill and comminuted using 0.3 mm yttria stabilized zirconia media until the maximum particle size was below 0.5 microns as indicated on a 0-12 micron indicating Hegman gauge with a 0.5 scale gradation. The resultant dispersion was pourable. The particle size of the sodium lignosulfonate particles in the dispersion was measured by static light scattering to be 0.169 microns with no particles detected below 0.1 microns.

Example 2

Dispersion of Sodium Lignosulfonate and Polyglyceryl-2 Dipolyhydroxystearate in Coco-Caprylate 30.0 parts by weight of sodium lignosulfonate (Vanisperse A, Borregaard LignoTech) was combined with 13.5 parts by weight of polyglyceryl-2 dipolyhydroxystearate and 56.5 parts by weight of coco-caprylate. The mixture was stirred until homogenous and transferred to a horizontal media mill and comminuted using 0.3 mm yttria stabilized zirconia media until the maximum particle size was below 0.5 microns as indicated on a 0-12 micron indicating Hegman gauge with a 0.5 scale gradation. The resultant dispersion was pourable.

Example 3

Dispersion of Sodium Lignosulfonate and Polyhydroxystearic Acid in Coco-Caprylate 30.0 parts by weight of sodium lignosulfonate (Vanisperse A, Borregaard LignoTech) was combined with 12.0 parts by weight of polyhydroxystearic acid and 58.0 parts by weight of coco-caprylate. The mixture was stirred until homogenous and transferred to a horizontal media mill and comminuted using 0.3 mm yttria stabilized zirconia media until the maximum particle size was below 0.5 microns as indicated on a 0-12 micron indicating Hegman gauge with a 0.5 scale gradation. The resultant dispersion was pourable.

Example 4

Dispersion of Sodium Lignosulfonate and Lecithin in Caprylic/Capric Triglycerides 30.0 parts by weight of sodium lignosulfonate (Vanisperse A, Borregaard LignoTech) was combined with 14.0 parts by weight of lecithin and 56.0 parts by weight of caprylic/capric triglycerides. The mixture was stirred until homogenous and transferred to a horizontal media mill and comminuted using 0.3 mm yttria stabilized zirconia media until the maximum particle size was below 0.5 microns as indicated on a 0-12 micron indicating Hegman gauge with a 0.5 scale gradation. The resultant dispersion was pourable.

Example 5

Dispersion of Sodium Lignosulfonate and Polyglyceryl-2 Dipolyhydroxystearate in C12-C15 Alkyl Benzoate 30.0 parts by weight of sodium lignosulfonate (Maracell XE, Borregaard LignoTech) was combined with 13.5 parts by weight of polyglyceryl-2 dipolyhydroxystearate and 56.5 parts by weight of C12-C15 alkyl benzoate. The mixture was stirred until homogenous and transferred to a horizontal media mill and comminuted using 0.3 mm yttria stabilized zirconia media until the maximum particle size was below 0.5 microns as indicated on a 0-12 micron indicating Hegman gauge with a 0.5 scale gradation. The resultant dispersion was pourable.

Example 6

Dispersion of 2:1 Mixture of Sodium Lignosufonate:Calcium Lignosulfonate and Polyglyceryl-2 Dipolyhydroxystearate in Caprylic/Capric Triglycerides 30.0 parts by weight of an approximately 2:1 mixture of sodium lignosulfonate:calcium lignosulfonate (Marasperse C-21, Borregaard LignoTech) was combined with 13.5 parts by weight of polyglyceryl-2 dipolyhydroxystearate and 56.5 parts by weight of caprylic/capric triglycerides. The mixture was stirred until homogenous and transferred to a horizontal media mill and comminuted using 0.3 mm yttria stabilized zirconia media until the maximum particle size was below 0.5 microns as indicated on a 0-12 micron indicating Hegman gauge with a 0.5 scale gradation. The resultant dispersion was pourable.

Example 7

Dispersion of Potassium Humate and Polyglyceryl-2 Dipolyhydroxystearate in Caprylic/Capric Triglycerides 30.0 parts by weight of potassium humate (Borregro HA-2, Borregaard LignoTech) was combined with 13.5 parts by weight of polyglyceryl-2 dipolyhydroxystearate and 56.5 parts by weight of caprylic/capric triglycerides. The mixture was stirred until homogenous and transferred to a horizontal media mill and comminuted using 0.3 mm yttria stabilized zirconia media until the maximum particle size was below 0.5 microns as indicated on a 0-12 micron indicating Hegman gauge with a 0.5 scale gradation. The resultant dispersion was pourable.

Example 8

Dispersion of Sodium Lignosulfonate and Cetyl Diglyceryl Tris(Trimethylsiloxy)Silylethyl Dimethicone in Caprylic/Capric Triglycerides 30.0 parts by weight of sodium lignosulfonate (Vanisperse A, Borregaard LignoTech) was combined with 13.5 parts by weight of cetyl diglyceryl tris(trimethylsiloxy)silylethyl dimethicone and 56.5 parts by weight of caprylic/capric triglycerides. The mixture was stirred until homogenous and transferred to a horizontal media mill and comminuted using 0.3 mm yttria stabilized zirconia media until the maximum particle size was below 0.5 microns as indicated on a 0-12 micron indicating Hegman gauge with a 0.5 scale gradation. The resultant dispersion was pourable.

Example 9 Comparative

Aqueous Slurry of Sodium Lignosulfonate and Alumina

An aqueous solution of sodium lignosulfonate was prepared as described in U.S. Pat. Nos. 6,500,411, 6,716,418 and U.S. Patent Application Publication No. 2010/0202985. 30 parts by weight of sodium lignosulfonate (Vanisperse A, Borregaard LignoTech) were added to 70 parts by weight of deionized water. The solution was stirred until the sodium lignosulfonate was completely dissolved. To this solution was added 60 parts by weight of submicron (0.42 micron D50 by volume as measured by static light scattering) tabular alumina (E390, Saint-Gobain). The resulting slurry was mixed using a disperser blade for 30 minutes. The resultant aqueous slurry was homogenous and readily pourable.

Example 10

Moisturizer with a Phenolic Polymer in the Oil Phase

A moisturizer composition was prepared as a water-in-oil emulsion including the dispersion of Example 1 in the oil phase. The ingredients of the moisturizer composition are shown below:

| Phase | Ingredient | % by weight |
|---|---|---|
| Oil Phase | polyglyceryl-2 dipolyhydroxystearate | 4.00 |
| | polyglyceryl-2 sesquioleate | 2.00 |
| | zinc stearate | 1.00 |
| | dispersion of Example 1 | 8.33 |
| | squalane | 2.00 |
| | C12-C15 alkyl benzoate | 20.82 |
| | coco-caprylate | 7.00 |
| Water Phase | water | 50.02 |
| | propanediol | 3.00 |
| | tetrasodium glutamate diacetate | 0.03 |
| | USP sodium chloride | 0.80 |
| | preservative | 1.00 |
| | TOTAL | 100.00 |

Using a cold process, the ingredients of the oil phase were combined and mixed until homogeneous, and, separately, the ingredients of the water phase were combined and mixed until homogeneous. The two phases were then combined and homogenized for 4 minutes at 5,000 RPM using a Ross HSM-100LC1 homogenizer. The resultant emulsion was stable after aging at 50° C. for 75 days and was very water resistant. The presence of the lipophillically dispersed phenolic polymer particles in the oil phase produced a moisturizer with HEV blocking and antioxidant properties.

Example 11

Moisturizing Sunscreen with a Phenolic Polymer in the Oil Phase

A sunscreen composition was prepared as a water-in-oil emulsion including the dispersion of Example 1 in the oil phase. The ingredients of the sunscreen composition are shown below:

| Phase | Ingredient | % by weight |
|---|---|---|
| Oil Phase | polyglyceryl-2 dipolyhydroxystearate | 4.000 |
| | polyglyceryl-2 sesquioleate | 2.000 |
| | zinc stearate | 1.000 |
| | dispersion of Example 1 | 8.330 |
| | squalane | 2.000 |
| | C12-C15 alkyl benzoate | 10.400 |
| | coco-caprylate | 7.000 |
| | USP zinc oxide | 10.000 |
| | triethoxycaprylylsilane | 0.175 |
| | polyhydroxystearic acid | 0.245 |
| Water Phase | water | 50.020 |
| | propanediol | 3.000 |
| | tetrasodium glutamate diacetate | 0.030 |
| | USP sodium chloride | 0.800 |
| | preservative | 1.000 |
| | TOTAL | 100.000 |

Using a cold process, the ingredients of the oil phase were combined and mixed until homogeneous, and, separately, the ingredients of the water phase were combined and mixed until homogeneous. The two phases were then combined and homogenized for 4 minutes at 5,000 RPM using a Ross HSM-100LC1 homogenizer. The resultant emulsion was stable after aging at 50° C. for 75 days and was very water resistant. The presence of the lipophillically dispersed phenolic polymer particles produced a moisturizing sunscreen with HEV blocking and antioxidant properties.

Example 12

Concealer Stick with a Phenolic Polymer in the Oil Phase (Prophetic)

A concealer stick composition is prepared as an anhydrous composition including the dispersion of Example 1. The ingredients of the concealer stick are shown below:

| Phase | Ingredient | % by weight |
|---|---|---|
| Phase A | coco caprylate | 16.27 |
| | propylheptyl caprylate | 17.00 |
| | dispersion of Example 1 | 8.33 |
| | titanium dioxide, disodium stearoyl glutamate, aluminum hydroxide | 7.00 |
| | iron oxides, disodium stearoyl, glutamate, aluminum hydroxide | 1.10 |
| Phase B | cetearyl alcohol | 5.00 |
| | hydrogenated castor oil | 6.00 |
| | pentaerythrityl distearate | 4.00 |
| | polyglyceryl-2 dipolyhydroxystearate | 1.00 |
| Phase C | talc | 29.80 |
| | aluminum starch octenylsuccinate | 3.00 |
| Phase D | preservative | 1.00 |
| Phase E | fragrance | 0.50 |
| | TOTAL | 100.000 |

Phase A is combined and mixed under high shear conditions. Phase B is added to Phase A and the mixture is heated to 85° C. under high shear conditions. Phase C is dispersed into the mixture under high shear conditions while maintaining the temperature at 85° C. The batch is then cooled under high shear mixing. Once the mixture cools to below 65° C., Phases D and E are added to the mixture step-wise under high shear mixing conditions. The batch is allowed to continue cooling until the temperature reaches 60° C. The batch is then dispensed into the final packaging. The presence of the lipophillically dispersed phenolic polymer particles produces a concealer stick with HEV blocking and antioxidant properties.

Example 13

HEV Blocking Study

The HEV blocking of the dispersion of Example 1 and the comparative aqueous slurry of Example 9 were compared. HEV blocking was measured using a diffuse transmission method similar to the methods described in 21 C.F.R. § 201.327 (Over-the-counter sunscreen drug products; required labeling based on effectiveness testing) and ISO 24443 (Determination of sunscreen UVA photoprotection in vitro).

1.3 mg/cm² of the dispersion of Example 1 was applied to the surface of an optical grade polymethylmethacrylate (PMMA) substrate having a roughened three-dimensional surface topography (LabSphere HelioPlate HD6). The dispersion was applied evenly to the surface of the substrate to correspond to a delivered dose of the phenolic polymer of 0.39 mg/cm². The aqueous slurry of Example 9 was applied in a similar manner to the substrate to correspond to a delivered dose of the phenolic polymer of 0.39 mg/cm².

The samples were visually inspected and both samples displayed a characteristic brown color associated with light absorption in the HEV region. The samples were then allowed to sit at room temperature for 1 hour. The absorbance of both samples and a control blank optical grade PMMA substrate were measured at the HEV wavelength of 450 nm using a LabSphere UV-2000S spectrophotometer. The net absorbance values were determined by subtracting the absorbance of the control blank substrate from the measured absorbance of the sample on the substrate.

The monochromatic protection factor (MPF) at 450 nm was determined according to the procedures in Bleasel, M. D. et al., "In vitro evaluation of sun protection factors of sunscreen agents using a novel UV spectrophotometric technique", International Journal of Cosmetic Science, Vol. 30, Issue 4, pp. 259-270 (2008). MPF may be expressed by Equation 2 below:

$$MPF(\lambda) = \frac{1}{10^{-A(\lambda)}} \qquad \text{Equation 2}$$

where $A(\lambda)$ is the net absorbance of the sample at wavelength $\lambda$.

The results are shown in the table below:

| Sample | Net absorbance (450 nm) | MPF (450 nm) |
| --- | --- | --- |
| Dispersion of Example 1 | 1.224 | 16.77 |
| Aqueous slurry of Example 9 | 0.711 | 5.14 |

The dispersion of Example 1 demonstrated a greater net absorbance and a greater MPF than the aqueous slurry of Example 9. These results indicate that phenolic polymers dispersed in an oil phase have superior HEV blocking as compared to aqueous slurries of phenolic polymers.

Example 14

Water Resistance Study

The water resistance of the dispersion of Example 1 and the comparative aqueous slurry of Example 9 were compared. Water resistance was measured using an 80-minute water immersion sequence consistent with COLIPA 2005 (Cosmetics Europe, "Guidelines for evaluating sun product water resistance", available online at www.cosmeticseurope.eu/files/7914/6407/7400/Guidelines_for_Evaluating_Sun_Product_Water_Resistance_-_2005.pdf, 15 pages (2005)) but performed in vitro.

A 22 cm high×16 cm diameter stainless steel vessel was filled with deionized water and maintained at a temperature between 30-33° C. The vessel was stirred at 350 RPM using a 5 cm diameter flat blade impeller throughout the duration of the test. Samples of the dispersion of Example 1 and the comparative aqueous slurry of Example 9 were suspended in the vessel near the wall of the vessel with the applied sample facing the impeller. The samples were removed from the vessel after 80 minutes of immersion and allowed to dry for 1 hour. The net absorbance and the monochromatic protection factor (MPF) were measured as described in Example 13. The results are shown in the table below:

| Measurement | Dispersion of Example 1 | Aqueous slurry of Example 9 |
| --- | --- | --- |
| Net absorbance (450 nm) before water immersion | 1.224 | 0.711 |
| MPF (450 nm) before water immersion | 16.77 | 5.14 |
| Net absorbance (450 nm) after water immersion | 1.167 | 0.012 |
| MPF (450 nm) after water immersion | 14.70 | 1.03 |
| % MPF maintained | 88 | 20 |

The Dispersion of Example 1 was able to maintain 95% of the net absorbance (450 nm) and retain 88% of the initial MPF (450 nm) value. These results indicate that the dispersion of Example 1 is very water resistant. Visual inspection revealed that the aqueous slurry of Example 9 lost the majority of the characteristic brown color associated with HEV attenuation 120 seconds into the immersion sequence. In addition, the aqueous slurry of Example 9 did not satisfy the requirements to be classified as very water resistant. These results demonstrate that lipophillically dispersed phenolic polymer particles in an oil phase have superior water resistance as compared to aqueous slurries of phenolic polymers.

Example 15

Free Radical Quenching and Photostability Study

The free radical quenching and photostability of the dispersion of Example 1 was investigated. Photostability was determined according to the modified DPPH photostability test (see Definitions section). Free radical quenching was determined according to the free radical quenching test (see Definitions section). Titanium dioxide was used as a comparative substance because it is known to be substantially non-photostable (photocatalytic) and generate copious photo-induced free radicals upon exposure to UV radiation.

Five photostability tests were carried out using varying amounts of the dispersion of Example 1 and the reference titanium dioxide. The results are shown in the table below:

| Test | % of phenolic polymer particles in the Dispersion of Example 1 | % $TiO_2$ | $\Delta E$ | Standard deviation |
|---|---|---|---|---|
| 1 | 0.115 | 0 | 0.65 | 0.441 |
| 2 | 0.0575 | 0.0575 | 3.91 | 0.166 |
| 3 | 0.115 | 0.115 | 1.01 | 0.082 |
| 4 | 0 | 0.115 | 18.84 | 1.104 |
| 5 | 0 | 0.0575 | 14.85 | 0.398 |

The results from test 1 demonstrate that the dispersion of Example 1 is super photostable. By comparison, an equal amount of the reference titanium dioxide (test 4) was not super photostable and produced 29 times the concentration of free radicals. Compositions containing equal amounts of the dispersion of Example 1 and titanium dioxide (tests 2 and 3) were super photostable, which shows that the dispersion of Example 1 actively quenches free radicals produced by the highly photoactive reference material by 73.7% to 94.7%. The dispersion of Example 1 passed the free radical quenching test at both weight percentages.

The results demonstrate that lipophillically dispersed phenolic polymer particles in an oil phase are super photostable and pass the free radical quenching test. The free radical quenching capability is an indication of the antioxidant properties of the lipophilic phenolic polymers. The results also show that lipophilic phenolic polymer particles can be combined with highly photoactive substances to produce super photostable compositions that protect users from UV-generated free radicals.

REFERENCES

1. U.S. Pat. No. 6,500,411.
2. U.S. Pat. No. 6,716,418.
3. U.S. Pat. No. 8,309,063.
4. U.S. Pat. No. 8,445,562.
5. U.S. Pat. No. 8,911,976.
6. U.S. Pat. No. 10,035,928.
7. U.S. Patent Application Publication No. 2007/0178057.
8. U.S. Patent Application Publication No. 2010/0202985.
9. U.S. Patent Application Publication No. 2015/0166836.
10. U.S. Patent Application Publication No. 2018/0291210.
11. International Patent Application Publication No. WO 2009/038477.
12. International Patent Application Publication No. WO 2014/144746.
13. International Patent Application Publication No. WO 2014/164418.
14. International Patent Application Publication No. WO 2017/197530.
15. Pan, X. et al., "Organosolv ethanol lignin from hybrid poplar as a radical scavenger: relationship between lignin structure, extraction conditions, and antioxidant activity", Journal of Agricultural and Food Chemistry, Vol. 54, pp. 5806-5813 (2006).
16. Cosmetics Europe, "Guidelines for evaluating sun product water resistance", available online at www.cosmeticseurope.eu/files/7914/6407/7400/Guidelines_for_Evaluating_Sun_Produc t_Water_Resistance_-_2005.pdf, 15 pages (2005).
17. Bleasel, M. D. et al., "In vitro evaluation of sun protection factors of sunscreen agents using a novel UV spectrophotometric technique", International Journal of Cosmetic Science, Vol. 30, Issue 4, pp. 259-270 (2008).
18. The International Lignin Institute, "About lignin", available online at www.ili-lignin.com/aboutlignin.php (accessed Aug. 30, 2019).

What is claimed is:

1. A composition, comprising:
   phenolic polymer particles, and
   a surfactant, on the phenolic polymer particles,
   wherein the composition is very water resistant.

2. The composition of claim 1, wherein the phenolic polymer particles comprise a substance selected from the group consisting of lignins, humates, tannins, botanical extracts containing water soluble and/or water dispersible components, and combinations thereof.

3. The composition of claim 1, wherein the surfactant comprises a substance selected from the group consisting of fatty alcohols and polyols, fatty acids, polyglyceryl esters, polyglyceryl polyesters, polyesters with affinic hydroxyl, amine or amide groups, polyurethanes with affinic hydroxyl, amine or amide groups, polyamides with affinic hydroxyl, amine or amide groups, polyacrylates with affinic hydroxyl, amine or amide groups, phosphate esters, polymeric phosphoric acid salts, phospholipids, ceramides, sphingosines, combinations thereof, copolymers thereof, and cross-polymers thereof.

4. The composition of claim 1, wherein the phenolic polymer particles have a particle size of 0.001-10.0 microns (μm).

5. A dispersion, comprising:
   the composition of claim 1, and
   a carrier vehicle.

6. The dispersion of claim 5, wherein the carrier vehicle comprises a substance selected from the group consisting of triglycerides, esters, natural oils and butters, alkanes, silicones and combinations thereof.

7. The dispersion of claim 5, wherein the phenolic polymer particles are present in an amount of 0.1-75.0% by weight, and
   The surfactant is present in an amount of 1.0-100.0% of the mass of the phenolic polymer particles.

8. A dispersion, comprising:
   sodium lignosulfonate particles,
   a surfactant on the sodium lignosulfonate particles, and
   a lipophilic cosmetically-acceptable fluid,
   wherein the sodium lignosulfonate particles have a particle size of 0.1-1.0 microns,
   the dispersion is pourable, and
   the dispersion is very water resistant.

9. The dispersion of claim 8, wherein the surfactant comprises polyglyceryl-2 dipolyhydroxystearate,
   the carrier vehicle comprises caprylic/capric triglycerides,
   the sodium lignosulfonate is present in an amount of 1.0-40.0% by weight, and
   the polyglyceryl-2 dipolyhydroxystearate is present in an amount of 15.0-50.0% by weight.

10. The dispersion of claim 9, wherein the dispersion is super photostable.

11. The dispersion of claim 9, wherein the dispersion passes the free radical quenching test.

12. A sunscreen composition, comprising:
    the composition of claim 1, and
    a UV radiation protectant.

13. The sunscreen composition of claim 12, wherein the UV radiation protectant is selected from the group consisting of zinc oxide (ZnO), titanium dioxide ($TiO_2$), p-aminobenzoic acid (PABA), padimate O, phenylbenzimidazole sulfonic acid, cinoxate (2-ethoxyethyl p-methoxycinnamate), dioxybenzone (benzophenone-8), oxybenzone (benzophenone-3), homosalate (homomethyl salicylate), menthyl anthranilate (meradimate), octocrylene (2-cyano-3,3-diphenyl acrylic acid), octyl methoxycinnamate (octinoxate), octyl salicylate (2-ethylhexyl salicylate), sulisobenzone (2-hydroxy-4-methoxybenzophenone-5-sulfonic acid, 3-benzoyl-4-hydroxy-6-methoxybenzenesulfonic acid, benzophenone-4), trolamine salicylate (triethanolamine salicylate), avobenzone (1-(4-methoxyphenyl)-3-(4-tert-butylphenyl)propane-1,3-dione), ecamsule (terephthalylidene dicamphor sulfonic acid), cerium oxide ($CeO_2$), drometrizole trisiloxane, bis-ethylhexyloxyphenol methoxyphenyl triazine, bisoctrizole and combinations thereof.

14. A method of protecting human skin, comprising:
applying the composition of claim 1 to the human skin.

15. Lipophilic phenolic polymer particles, wherein the lipophilic phenolic polymer particles are very water resistant.

16. A method of treating or preventing oxidative damage to skin, comprising:
applying the composition of claim 1 to the skin.

17. A method of protecting keratinous material, comprising:
applying the composition of claim 1 to the keratinous material,
wherein the keratinous material is selected from the group consisting of hair, fingernails, toenails, and the outer layer of skin.

18. A method of suppressing lipid peroxidation in the skin, comprising:
applying the composition of claim 1 to the skin.

19. A method of preventing or reducing the appearance of lines and wrinkles in skin, comprising:
applying the composition of claim 1 to the skin.

20. A method of preventing loss of elasticity of skin, comprising:
applying the composition of claim 1 to the skin.

21. A method of preventing thinning of skin, comprising:
applying the composition of claim 1 to the skin.

22. A method of preventing pigment darkening of skin, comprising:
applying the composition of claim 1 to the skin.

23. A method of attenuating HEV radiation exposure to skin, comprising:
applying the composition of claim 1 to the skin.

24. A method of quenching free radicals in keratinous material, comprising:
applying the composition of claim 1 to the keratinous material,
wherein the keratinous material comprises hair or skin.

* * * * *

UNITED STATES PATENT AND TRADEMARK OFFICE
CERTIFICATE OF CORRECTION

| | |
|---|---|
| PATENT NO. | : 11,155,683 B2 |
| APPLICATION NO. | : 16/570944 |
| DATED | : October 26, 2021 |
| INVENTOR(S) | : Harry W. Sarkas et al. |

It is certified that error appears in the above-identified patent and that said Letters Patent is hereby corrected as shown below:

In the Claims

Column 16, Line 54, please delete "carrier vehicle" and insert --lipophilic cosmetically-acceptable fluid--

Signed and Sealed this
Fourth Day of April, 2023

Katherine Kelly Vidal
*Director of the United States Patent and Trademark Office*